Nov. 21, 1939. J. A. WORKMAN Plant Pat. 347
ORANGE TREE
Filed May 5, 1939
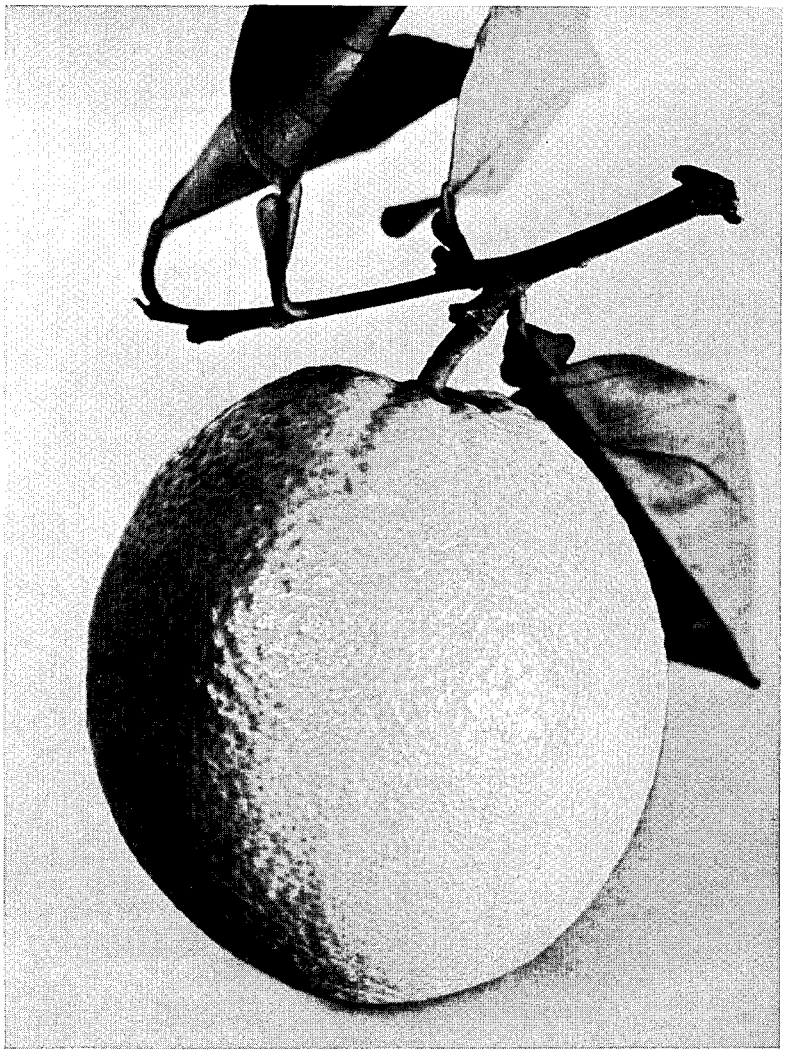
John Albert Workman
INVENTOR
By Orville M. Kile
PLANT PATENT AGENT Patented Nov. 21, 1939

Plant Pat. 347

UNITED STATES PATENT OFFICE

347

ORANGE TREE

John Albert Workman, Riverside, Calif., assignor to Armstrong Nurseries, Ontario, Calif.

Application May 5, 1939, Serial No. 272,023

1 Claim. (Cl. 47—62)

My new variety of orange tree is of the class known as navel oranges and is an improvement over the well-known commercial variety, the Washington Navel Orange. It originated as a bud sport limb on a Washington Navel Orange tree located on my property at Riverside, California. The parent tree is about twenty-five years old and the sport discovered by me several years ago has since been the subject of observation, tests and experimentation. I noticed that the fruit on this limb remained in good condition several months after the other fruit had been picked. The new variety has been asexually reproduced by budding and remains true to type.

The accompanying illustration shows a single fruit of my new variety, together with portions of the stem and leaves.

My new variety is more nearly like the Washington Navel Orange than any other variety known to me. However, there are several very marked differences between the two varieties. Since the Washington Navel Orange is well known, this new variety can best be described by comparing it with the parent variety and pointing out the differences.

The matured fruits of these two varieties appear to be approximately alike in the matter of size, form, texture, thickness of rind, flavor and amount of juice. However, the fruits mature at very different dates when grown side by side under the same conditions. The fruits of the new variety remain green until after the first of January, while the fruits of the original tree and other tress of the Washington Navel variety are well colored by December first in normal years. The fruits of the Washington Navel Orange seldom hang on the tree after the month of June, but the fruits of this new variety hang on at least until September and have been observed in good condition as late as November. The fruits of the new variety mature two to three months later than those of the Washington Navel Orange so far as flavor, amount of sugar and color are concerned, and the period of time they hang on the tree is two to three months longer than for those of the Washington Navel Orange. The season of ripening is April to September for the new variety as compared with a season of ripening from December to May for the Washington Navel Orange.

The flowers of this new variety are similar to those of the Washington Navel Orange and appear in May as compared to the April appearance of the latter.

The foliage of this new variety is somewhat larger and more dense than that of the Washington Navel Orange. The leaves are broader at the tips, have a smaller amount of serration, and their petioles are usually much broader.

The tree is an upright grower of moderate vigor—slightly more vigorous than the Washington Navel Orange tree.

Following is a somewhat detailed description of this new variety, particularly as pertains to the fruits and leaves.

Tree:
- Upright; moderately vigorous; semi-dwarf; practically thornless.

Foliage:
- Large, dense.
- *Leaves.*—Elliptical to oblong ovate, acuminate to mucronate at tips, entire at base, sometimes slightly serrate toward the tip; 3 to 4 inches long, smooth, shining, lighter below than above. Petiole—usually broadly winged.

Flowers:
- Normal except that the anthers are cream colored and are absolutely without pollen. (Just as in the case of the Washington Navel Orange.)

Fruit:
- *Form.*—Rounded; slightly tapering toward apex and terminating in an umbilicus which is usually of small size.
- *Size.*—Three to three and one-fourth inches in diameter.
- *Rind.*—Smooth to slightly pebbled due to large oil cells; firm; one-eighth to one-fourth inch thick; easily separated from flesh.
- *Locules.*—Eight to twelve; easily separated from each other.
- *Flesh.*—Deep orange-yellow with tender rag; excellent quality.
- *Juice sacs.*—Large and spindle-shaped.
- *Juice.*—Abundant and of excellent flavor in which acidity and sweetness are well blended.
- *Seeds.*—Absent.

Having thus disclosed my discovery, I claim:

A new and distinct variety of navel orange tree substantially as described, characterized particularly by its greater vigor; its denser foliage composed of slightly larger, less serrate and broader leaves; its later flowering season; and the much later season of maturity of its fruit; all as compared with the Washington Navel Orange.

JOHN ALBERT WORKMAN.